US009784702B2

(12) United States Patent
Seok et al.

(10) Patent No.: US 9,784,702 B2
(45) Date of Patent: Oct. 10, 2017

(54) APPARATUS FOR CONTINUOUSLY TESTING THERMAL FATIGUE

(71) Applicant: Research & Business Foundation SUNGKYUNKWAN UNIVERSITY, Suwon-si (KR)

(72) Inventors: Changsung Seok, Gwacheon-si (KR); Jeongmin Lee, Ansan-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 386 days.

(21) Appl. No.: 14/621,754

(22) Filed: Feb. 13, 2015

(65) Prior Publication Data

US 2015/0233850 A1    Aug. 20, 2015

(30) Foreign Application Priority Data

Feb. 14, 2014   (KR) .................. 10-2014-0017220

(51) Int. Cl.
*G01N 25/72*   (2006.01)
(52) U.S. Cl.
CPC .................................. *G01N 25/72* (2013.01)
(58) Field of Classification Search
CPC ............................. G01N 25/00; G01N 25/72
See application file for complete search history.

(56) References Cited

U.S. PATENT DOCUMENTS 9,377,419 B2 *   6/2016   Las Navas Garcia .   G01N 5/045
9,546,969 B2 *   1/2017   Las Navas Garcia ...   G01N 1/44

FOREIGN PATENT DOCUMENTS

JP          55-135730 A     10/1980
JP          2005-121256 A    5/2005
JP          2006-292523 A   10/2006

* cited by examiner

*Primary Examiner* — Randy Gibson
(74) *Attorney, Agent, or Firm* — NSIP Law

(57) ABSTRACT

An apparatus for continuously testing thermal fatigue may include: a rotating member which is rotated about a central axis and which is provided with a plurality of protrusions outwardly protruded from an outer surface of the rotating member, the plurality of protrusions being formed along a virtual circle having a central portion passing through the central axis and coated specimens being installed on the end portion of the protrusions; and a heating part which is provided to receive a portion of a rotating path of the specimens therein and which is provided with a heating groove inwardly recessed from a surface of the heating part facing the rotating member along the rotating path of the specimens so as to heat the specimens within the heating part, wherein the rotating path of the specimens includes a heating section which is received in the heating groove and a cooling section which is not received in the heating groove.

19 Claims, 9 Drawing Sheets

APPARATUS FOR CONTINUOUSLY TESTING THERMAL FATIGUE

CROSS-REFERENCE TO RELATED APPLICATION

This application claims the benefit of priority under 35 U.S.C. §119(a) of Korean Patent Application No. 10-2014-0017220, filed on Feb. 14, 2014, in the Korean Intellectual Property Office, the entire disclosure of which is incorporated herein by reference for all purposes.

FIELD

The present invention relates to an apparatus for continuously testing thermal fatigue, and more particularly, to an apparatus for continuously testing thermal fatigue, capable of simultaneously performing a thermal fatigue test on a plurality of specimens by continuously heating and cooling the plurality of specimens.

BACKGROUND

In general, high temperature components of gas turbine generators which is being operated at a temperature of 1,100° C. or greater may be exposed to high-temperature and high-pressure combustion gas and have been used in environmental conditions where a mechanical stress is applied by 3,600 revolutions per minute (RPM).

In particular, since gas turbine generators are operated while a starting-up operation and a stopping operation thereof are repeated every day, the high temperature components may be repeatedly heated and cooled, whereby inherent material characteristics of the high temperature components may be further rapidly degraded.

In order to prevent a deterioration in material characteristics of the high temperature components, in the case of a component fabricated using a further excellent material or a surface-treated component, it may be required to prove stability of the component by performing a test thereon before it is actually applied to the gas turbine generators.

Among tests for examining stability of components, a representative example may be a heat cycle test.

That is, the heat cycle test may be conducted by repeating a step in which a user directly inputs specimens in a space maintained at high temperature and takes out the specimens therefrom after the elapse of a predetermined time to thereby cool the specimens, or by using an apparatus for testing thermal fatigue or an apparatus for testing thermal tension.

However, it may be infeasible to perform thermal fatigue and tension tests at an actual operating temperature of a gas turbine, it may be unviable to test several specimens under the same conditions, and the rapid cooling of the specimens may be difficult.

As the related art technology for solving the above problem, Korean Utility Model Registration Publication No. 20-0406102 teaches "an apparatus for testing thermal fatigue".

In Korean Utility Model Registration Publication No. 20-0406102, FIG. 1 is a conceptual diagram schematically illustrating the apparatus for testing thermal fatigue.

Referring to FIG. 1 of Korean Utility Model Registration Publication No. 20-0406102, an apparatus 10 for testing thermal fatigue according to the related art may be provided to measure thermal fatigue strength of a high temperature component specimen used in a gas turbine generator, and may include a tube furnace 1 heating specimens (not shown) to high temperature, a cooling part (not shown) rapidly cooling the heated specimens to room temperature, a specimen transferring element allowing the specimens to be installed thereon and transferring the specimens to the tube furnace 1 or the cooling part, and a controlling unit controlling temperatures and times of the tube furnace 1 and the cooling part and the repeated numbers of times.

In addition, the specimen transferring element may include a specimen mounting part 7 allowing the specimens to be mounted thereon and transferring the specimens to the tube furnace 1 and the cooling part, and an air cylinder part 5 driving the specimen mounting part 7, and the cooling part may include an air compressor 3 and a compressed air spraying nozzle 4.

That is, in the apparatus 10 for testing thermal fatigue according to the related art, after six specimens are simultaneously mounted in holes of the specimen mounting part 7, a switch of a control panel 8 may be operated to drive the air cylinder part 5, and the specimen mounting part 7 may be carried into a quartz pipe 2.

In this state, the specimens are maintained at high temperature for a preset time as required. After the elapse of the preset time, the specimen mounting part 7 may be taken out and may be transferred to a lower portion of the compressed air spraying nozzle 4 connected to the air compressor 3.

In this state, compressed air may be sprayed out and may be rapidly cooled to room temperature. The heating and cooling is regarded as a single cycle and the heating and cooling may be repeatedly performed in required numbers of cycles.

However, in the apparatus 10 for testing thermal fatigue according to the related art, since a test specimen is heated at the same temperature over an overall thickness thereof, time required for reaching thermal fatigue fracture may be extended, such that test efficiency may be significantly deteriorated.

Moreover, in the apparatus 10 for testing thermal fatigue according to the related art, during a thermal fatigue test, a laser beam or flames are used as a thermal source to directly heat a coating layer, and an opposite side of the test specimen may be cooled by spaying compressed air thereto or bringing the opposite side into contact with a block in which cooling water circulates, such that a thermal gradient may be applied. However, in this case, it may be difficult to control a flame temperature and positon and costs required for manufacturing the apparatus and examining a test may be disadvantageously high.

SUMMARY

An object of the present invention is to provide an apparatus for continuously testing thermal fatigue, capable of simultaneously performing a thermal fatigue test on a plurality of specimens by continuously heating and cooling the plurality of specimens.

According to an aspect of the present invention, an apparatus for continuously testing thermal fatigue may include: a rotating member which is rotated about a central axis and which is provided with a plurality of protrusions outwardly protruded from an outer surface of the rotating member, the plurality of protrusions being formed along a virtual circle having a central portion passing through the central axis and coated specimens being installed on the end portion of the protrusions; and a heating part which is provided to receive a portion of a rotating path of the specimens therein and which is provided with a heating groove inwardly recessed from a surface of the heating part facing the rotating member along the rotating path of the specimens so as to heat the specimens within the heating part, wherein the rotating path of the specimens includes a heating section which is received in the heating groove and a cooling section which is not received in the heating groove.

The heating groove may be provided with an inlet into which the specimens in a cooled state are introduced and an outlet from which the specimens in a heated state are discharged, and the apparatus may further include an air-curtain formation part which is disposed on at least one of the inlet and the outlet to form an air-curtain so as to minimize the occurrence of a thermal transfer through the heating groove.

The apparatus may further include: a controller which controls at least one of a rotational speed and a rotational direction of the rotating member.

The rotating member may be sequentially rotated in one direction or an opposite direction thereto by the controller.

The heating part may be provided as a plurality of heating parts which are spaced apart from each other along a rotating path of the protrusions, and the cooling section may be formed in each space between the plurality of heating parts.

The protrusions may be formed along virtual circles which have a common central portion passing through the central axis while having different diameters, and the heating groove may be provided as a plurality of grooves which are formed to be spaced apart from each other in a direction toward a central portion of the heating part or in a radial direction so as to correspond to the protrusions.

The apparatus may further include: a cooling fluid spraying part which sprays a cooling fluid to the cooling section so as to cool the specimens on the cooling section.

The cooling fluid spraying part may spray water or compressed air, or may simultaneously spray water and compressed air.

The apparatus may further include: a cooling part which receives the cooling section therein and which is provided with a cooling groove inwardly recessed from a surface of the cooling part facing the rotating member along the rotating path of the specimens so as to cool the specimens within the cooling part.

According to another aspect of the present invention, a method for continuously testing thermal fatigue on the coated specimens, using the above apparatus, may include: a specimen-installing step to install the specimens on the upper portion of the protrusions; a heating part-heating step to heat the heating part to a predetermined temperature; a specimen-heating step to provide the specimens installed on the upper portion of the protrusions into the heating groove by rotating the rotating member and to heat the specimens; a specimen-cooling step to allow the specimens present in the interior of the heating groove to be exposed outwardly from the heating part by rotating the rotating member and to cool the specimens; and a repeating step to repeatedly perform the specimen-heating step and the specimen-cooling step until the coating of the specimens is delaminated.

BRIEF DESCRIPTION OF DRAWINGS

The above and other aspects, features and other advantages of the present invention will be more clearly understood from the following detailed description taken in conjunction with the accompanying drawings, in which.

DETAILED DESCRIPTION

Figure 1:
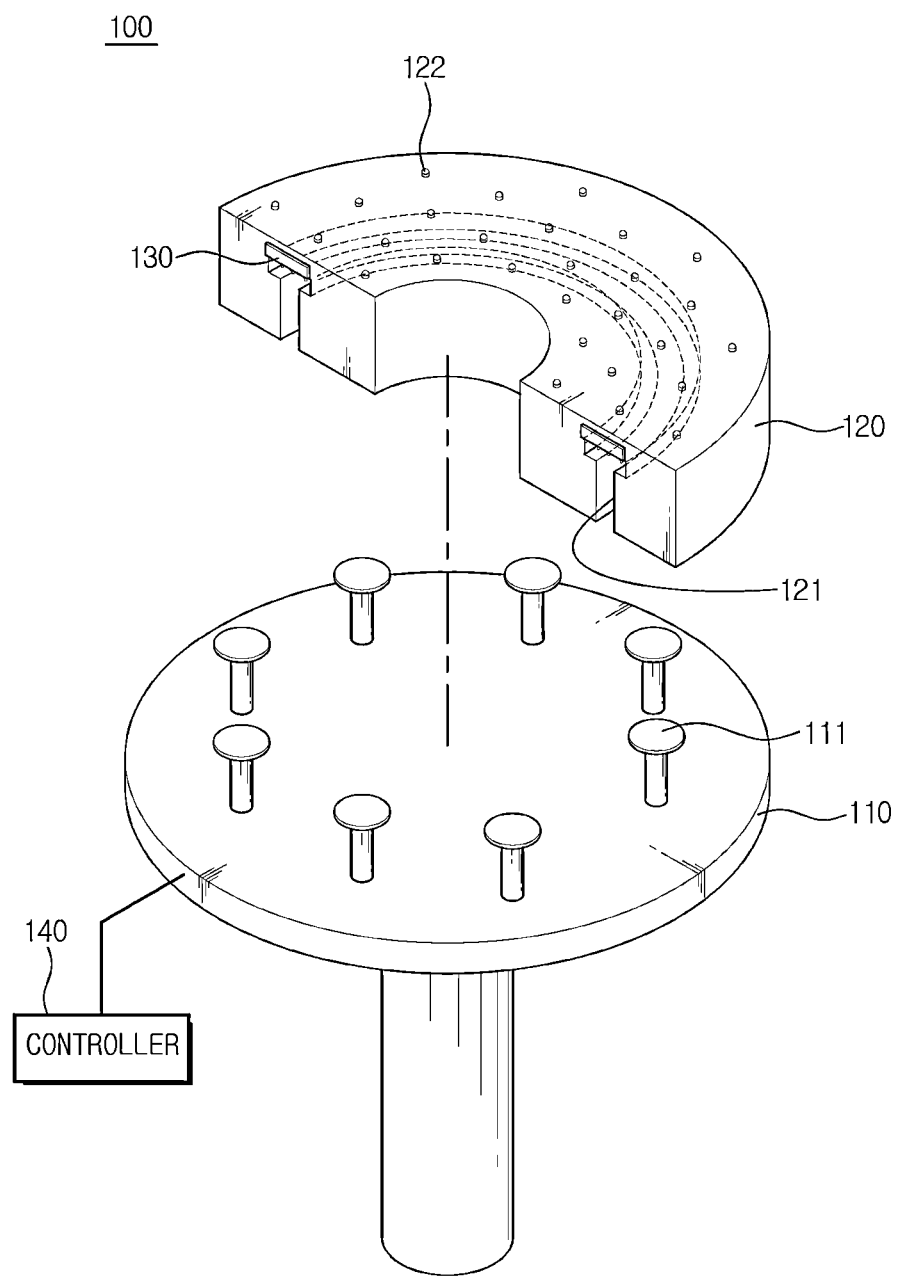
FIG. 1 is an exploded perspective view schematically illustrating an apparatus for continuously testing thermal fatigue according to a first exemplary embodiment of the present invention.

Exemplary embodiments of the present invention will now be described in detail with reference to the accompanying drawings.

The disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

In the drawings, the shapes and dimensions of elements may be exaggerated for clarity, and the same reference numerals will be used throughout to designate the same or like elements.

Prior to the description, in several embodiments, components having the same configurations will be described using the same reference numerals representatively in a first exemplary embodiment, and other components different from those of the first exemplary embodiment will be described in other exemplary embodiments.

Hereinafter, an apparatus 100 for continuously testing thermal fatigue according to a first exemplary embodiment of the present invention will be described in detail with reference to the attached drawings.

In the first exemplary embodiment, specimens S, test subjects for a thermal fatigue test, may be members respectively having coated outer surfaces. Accordingly, a time at which a coating of the specimen (test piece) S is peeled off during a period in which the thermal fatigue test is performed is regarded as a completion time of the thermal fatigue test, and the thermal fatigue test on the specimen S may be continuously conducted until the coating is peeled off.

Figure 2:
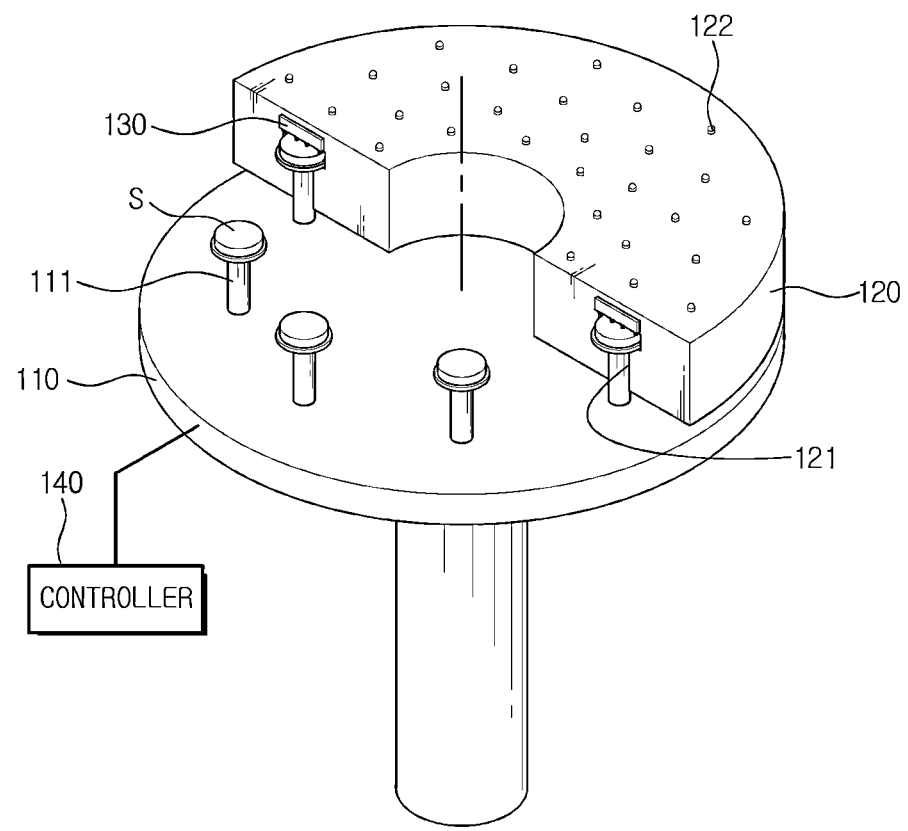
FIG. 2 is a perspective view schematically illustrating the apparatus for continuously testing thermal fatigue of FIG. 1.

FIG. 1 is an exploded perspective view schematically illustrating an apparatus for continuously testing thermal fatigue according to a first exemplary embodiment of the present invention. FIG. 2 is a perspective view schematically illustrating the apparatus for continuously testing thermal fatigue of FIG. 1.

Referring to FIG. 1 or 2, the apparatus 100 for continuously testing thermal fatigue according to the first exemplary embodiment of the present invention may simultaneously perform a thermal fatigue test on a plurality of specimens, and may include a rotating member 110, a heating part 120, an air-curtain formation part 130, and a controller 140.

The rotating member 110 which is a member rotatably provided about a central axis C may be formed along a virtual circle having a central portion thereof passing through the central axis and may be provided with protrusions 111 outwardly protruded from an outer surface of the rotating member 110, the specimens being installed on upper portions of the protrusions 111.

In this case, the rotating member 111 may rotate by being connected to a separate motor, but is not limited thereto. It goes without saying that the rotating member 111 may be connected to a constitution well known in the art, capable of implementing a rotational motion to thereby perform a rotating operation.

Meanwhile, in the first exemplary embodiment of the present invention, since the rotating member 110 may be disposed below the heating part 120 to be described later, the protrusions 111 may be protruded upwardly from an upper surface of the rotating member 110.

In addition, the specimen S may be installed on the upper portion of the protrusions 111, more accurately, on the upper surface of the protrusions 111 and may rotate together with rotation of the rotating member 110.

Meanwhile, in the first exemplary embodiment, the specimens may further include separate elements capable of fixing the specimens onto the upper surfaces of the protrusions 111.

Figure 3:
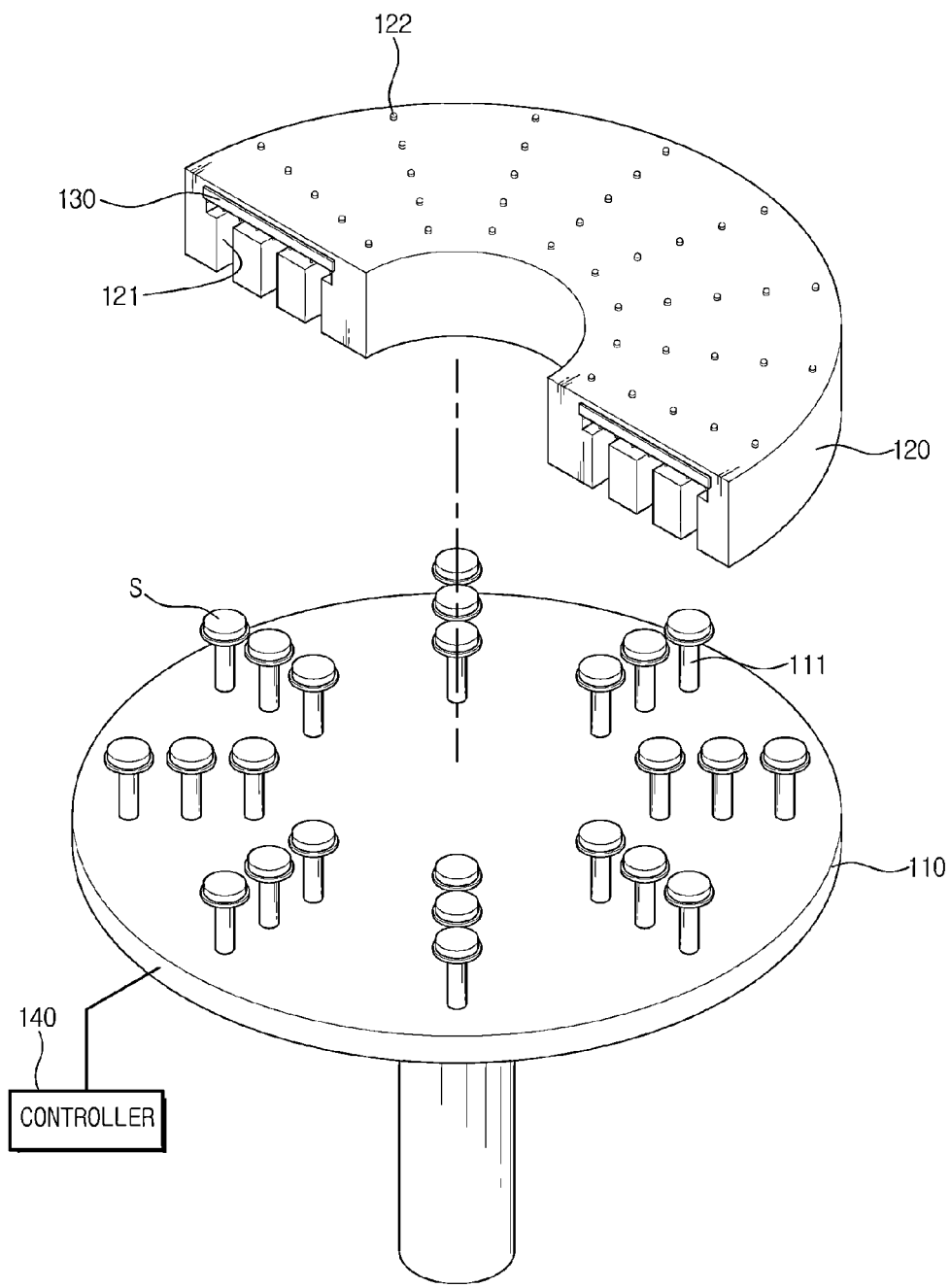
FIG. 3 is an exploded perspective views schematically illustrating a modified example of the apparatus for continuously testing thermal fatigue of FIG. 1.

FIG. 3 is an exploded perspective view schematically illustrating a modified example of the apparatus for continuously testing thermal fatigue illustrated in FIG. 1.

Referring to FIG. 3, the protrusions 111 may be protruded upwardly from the upper surface of a plurality of virtual circles having central portions passing through the central axis of the rotating member 110.

The heating part 120 may be provided to receive a portion of a rotating path of the specimens S therein and may heat the specimens S when the specimens S are received in the interior of the heating part 120. The heating part 120 may be provided with a heating groove 121 inwardly recessed from a surface of the heating part 120 which faces the protrusions 111.

Here, methods of heating the heating part 120 may be variously present. The first exemplary embodiment of the present invention employs a scheme of heating the heating part 120 through heating elements 122 by installing the heating elements 122 on the heating part 120. It goes without saying that methods of heating the heating part 120 are not limited thereto.

Figure 5:
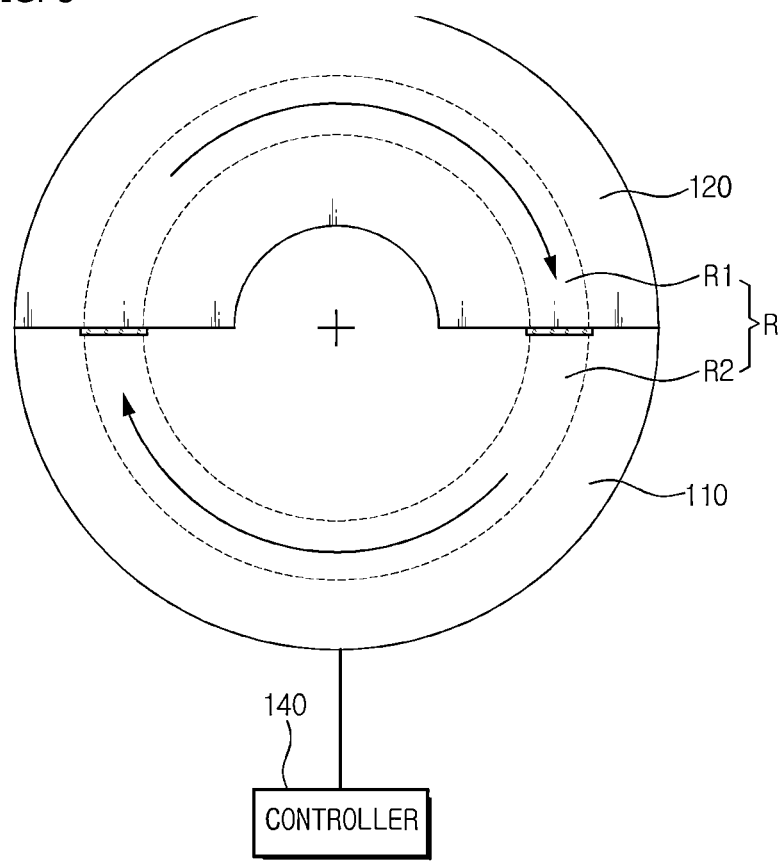
FIG. 5 is a plan view schematically illustrating a transfer path of specimens in the apparatus for continuously testing thermal fatigue of FIG. 1.

FIG. 5 is a plan view schematically illustrating a moving path of specimens in the apparatus for continuously testing thermal fatigue of FIG. 1.

Referring to FIG. 5, the rotating path of the specimens S may include a heating section R1 in which the specimens are heated and a cooling section R2 in which the specimens are cooled.

The heating section R1 may be determined by a shape of the heating part 120. In other words, the heating section R1 is a section which is received by the heating part 120 in the rotating path of the specimens S. The heating section R1 may have a cross-sectional shape substantially identical to that of the heating groove 121. The reason for this is that the specimens S are heated while the specimens S move inside the heating groove 121.

The cooling section R2 may be determined by the shape of the heating part 120 and may be a section which is not received by the heating part 120 in the rotating path of the specimens S.

The heating part 120 may be provided to have a shape of a semicircle having a concentric axis with the rotating member 110 in the first exemplary embodiment of the present invention. Alternatively, the heating part 120 may be provided in plural and the plurality of heating parts 120 may be provided to have fan shapes or circular-sector shapes whose central angle is 90° or less.

Referring to FIGS. 2 and 5, the semicircular shaped heating part 120 is shown.

That is, in the case that the heating part 120 is provided in a semicircular shape, the heating section R1 may be provided in an arc shape corresponding to the shape of the heating part 120, and the cooling section R2 may be provided in the remainder arc shape excluding the shape of the heating part 120.

Figure 4:
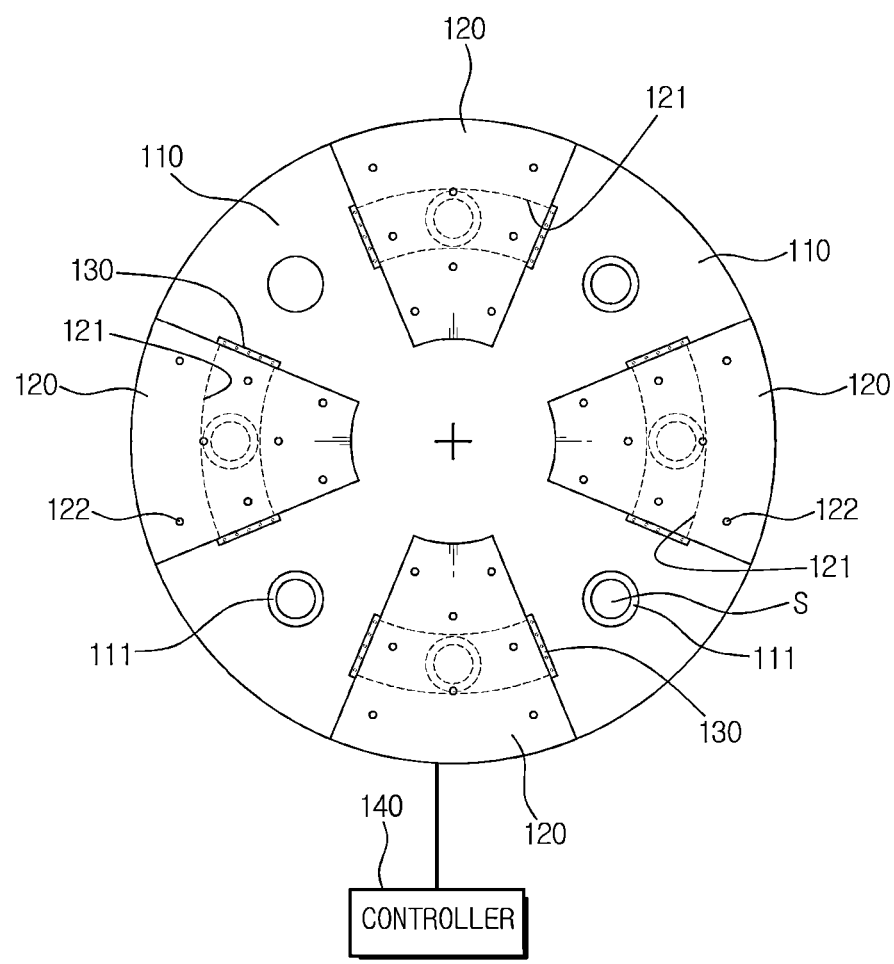
FIG. 4 is a plan view schematically illustrating another modified example of the apparatus for continuously testing thermal fatigue of FIG. 1.

FIG. 4 is a plan view schematically illustrating another modified example of the apparatus for continuously testing thermal fatigue illustrated in FIG. 1.

Referring to FIG. 4, in the case that the heating part 120 is provided as a plurality of heating parts 120 having fan shapes, a plurality of heating sections R1 having an arc shape corresponding to the shape of the heating parts 120 may be provided, and cooling sections R2 may be provided as remaining regions not corresponding to the shape of the heating parts 120. In this case, the heating sections R1 and the cooling sections R2 may be alternately disposed in a repeated manner in a single virtual circle.

The heating groove 121 may be provided with an inlet 121a into which the specimen S in a cooled state is introduced and an outlet 121b from which the specimen S in a heated state is discharged, and positions of the inlet 121a and the outlet 121b may coincide with points at which the heating sections R1 and the cooling sections R2 contact each other.

Figure 6:
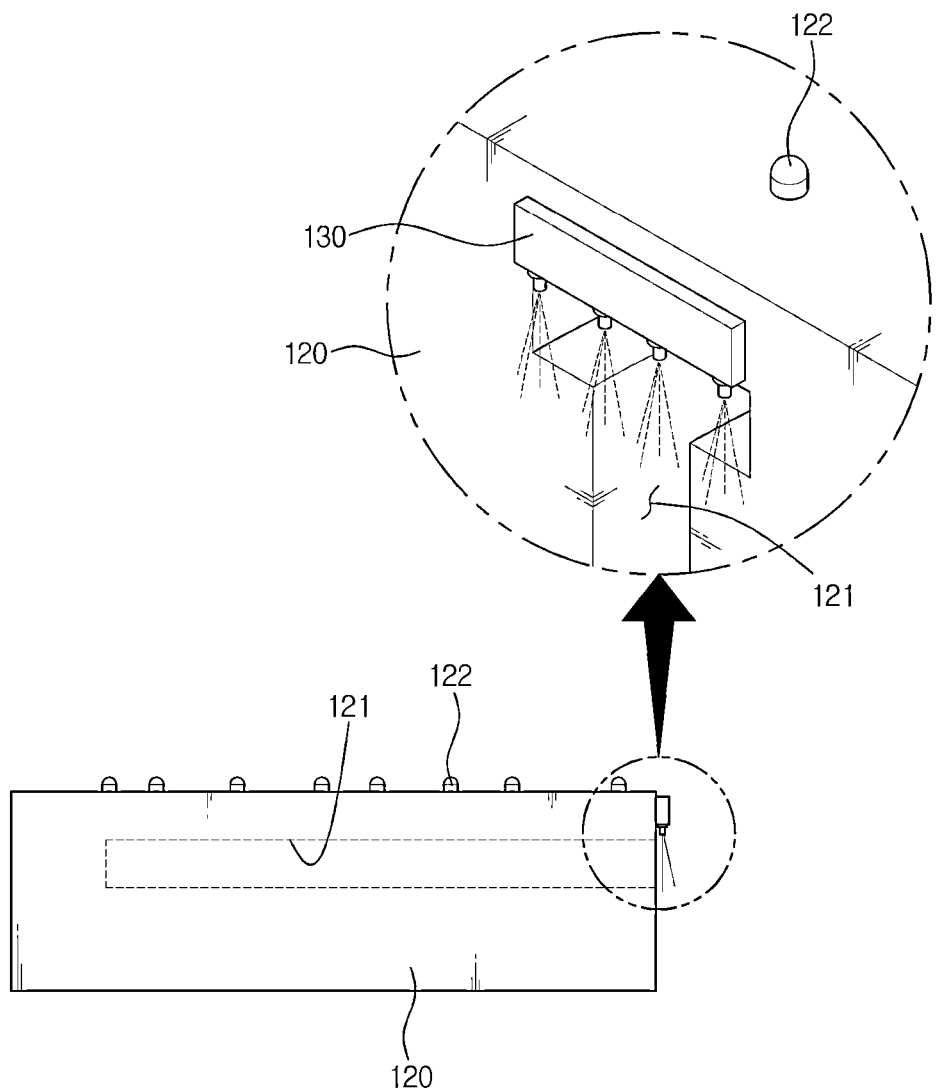
FIG. 6 is a view schematically illustrating an air-curtain formation part in the apparatus for continuously testing thermal fatigue of FIG. 1.

FIG. 6 is a view schematically illustrating an air-curtain formation part in the apparatus for continuously testing thermal fatigue of FIG. 1.

Referring to FIG. 6, the air-curtain formation part 130 may be disposed on at least one of the inlet 121a and the outlet 121b and may form an air-curtain on at least one of the inlet 121a and the outlet 121b so as to significantly reduce the introduction of external air or the like into the heating groove 121.

Here, the term "the formation of an air-curtain" means forming an air film using compressed air to thereby block air flow between the inner part and the outer part.

In the present invention, since the heating groove 121 may be opened to the outside and external factors hindering heating may be introduced into the heating groove 121, it is necessary to block the inlet 121a and the outlet 121b of the heating groove 121 from the outside.

Thus, an air-curtain may be formed on at least one of a boundary between the inlet 121a and the outside and a boundary between the outlet 121b and the outside by the air-curtain formation part 130, such that the inlet 121a and the outlet 121b of the heating groove 121 may be blocked from the outside.

Meanwhile, the air-curtain formation part 130 according to an exemplary embodiment of the present invention is not limited to a specific device, as long as it may form an air-curtain.

The controller 140 may control at least one of a rotational speed and a rotational direction of the rotating member 110 and consequently, may determine a heating period and a cooling period of the specimens S.

In other words, controlling the rotational speed and the rotational direction of the rotating member 110 may determine a time for which the specimens S stay within the heating groove 121 and a time for which the specimens S are opened to the outside in the cooing section R2. Consequently, the above time may determine the heating period and the cooling period.

In addition, the controller 140 may control the rotational direction of the rotating member 110, whereby the rotating member 110 may be sequentially rotated in one direction and an opposite direction thereto.

That is, the controller part 140 may convert the rotational direction of the rotating member 110 by a predetermined interval to thereby extend or shorten a heating path or a cooling path of the specimens S.

Meanwhile, according to the first exemplary embodiment, the apparatus for continuously testing thermal fatigue may further include a cooling fluid spraying part 150 spraying a cooling fluid to the cooling section R2 so as to further efficiently cool the specimens S while the specimens S move along the cooling section R2.

Figure 7:
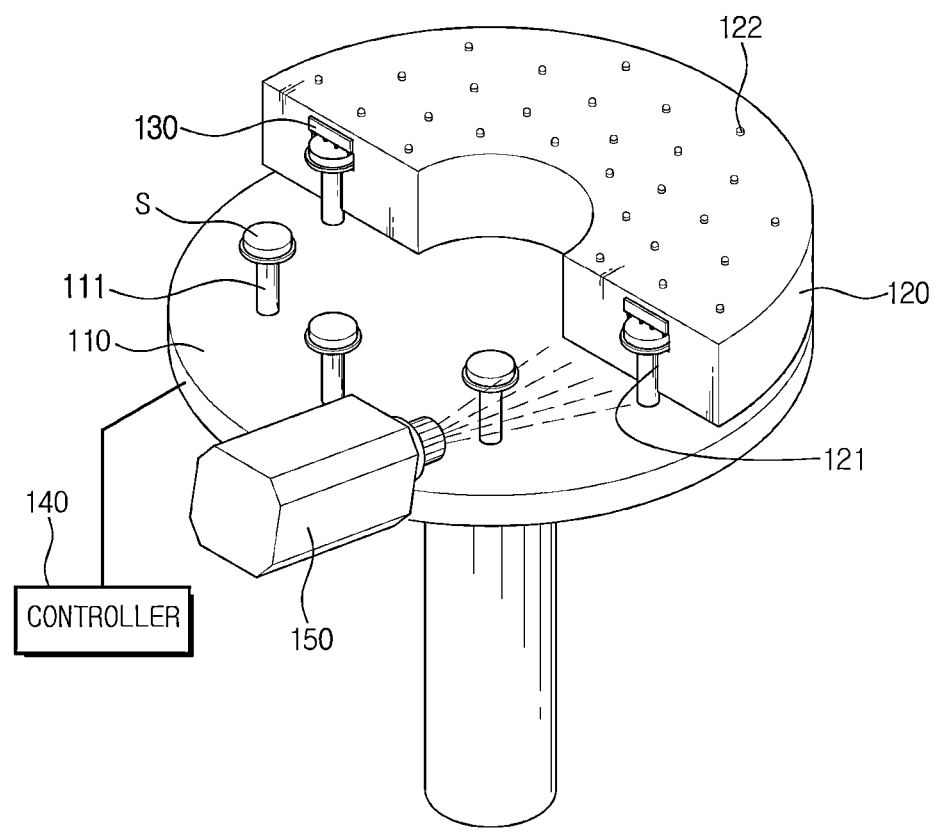
FIG. 7 is a perspective view schematically illustrating a state in which a cooling fluid is sprayed into a cooling section through a cooling fluid spraying part in the apparatus for continuously testing thermal fatigue of FIG. 1.

FIG. 7 is a perspective view schematically illustrating a state in which a cooling fluid is sprayed on a cooling section through a cooling fluid spraying part in the apparatus for continuously testing thermal fatigue of FIG. 1.

Referring to FIG. 7, in the case that a difference between a temperature of the heating section R1 and a temperature of the cooling section R2 is insignificant, it may be difficult to cool the specimens S to a degree to which a user intends in some cases. In order to solve the problem, the apparatus for continuously testing thermal fatigue may further include the cooling fluid spraying part 150 to forcibly cool the specimens S.

In this case, a fluid sprayed from the cooling fluid spraying part 150 may be water, compressed air or a combination thereof.

Hereinafter, a testing method of the apparatus 100 for continuously testing thermal fatigue according to a first exemplary embodiment of the present invention will be described.

Figure 8:
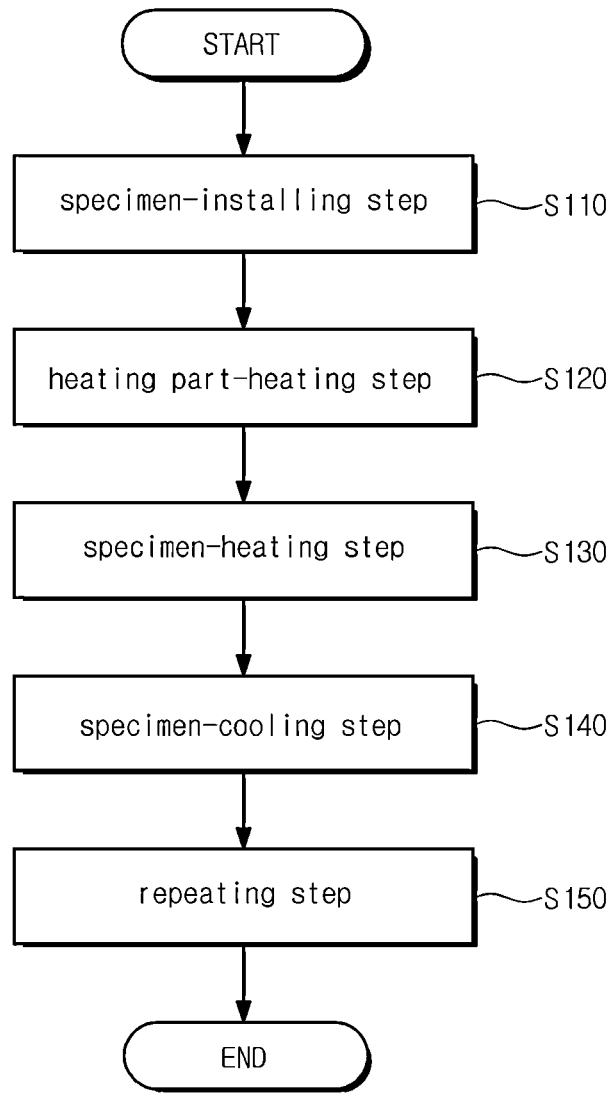
FIG. 8 is a flow chart schematically illustrating a method for testing thermal fatigue according to a first exemplary embodiment of the present invention.

FIG. 8 is a flow chart schematically illustrating a method for continuously testing thermal fatigue according to a first exemplary embodiment of the present invention.

Referring to FIG. 8, a method S100 for continuously testing thermal fatigue according to a first exemplary embodiment of the present invention may include a specimen-installing step S110, a heating part-heating step S120, a specimen-heating step S130, a specimen-cooling step S140, and a repeating step S150.

Meanwhile, prior to the description of the method S100 for continuously testing thermal fatigue according to the first exemplary embodiment of the present invention, for convenience of explanation, a description is made on the assumption that a single specimen S may be installed on each of the protrusions 111 of the apparatus 100 for continuously testing thermal fatigue.

The specimen-installing step S110 is a step to install the specimen S, a subject for testing thermal fatigue, on the upper portion of the protrusion 111. Since the protrusion 111 is formed on the rotating member 110, it may rotate together with the rotating member 110, such that the specimen S may pass through the heating section in the heating part 120 and the cooling section outside of the heating part 120.

The heating part-heating step S120 is a step to heat the heating part 120 to a predetermined temperature. Here, the predetermined temperature is a temperature to be tested in the thermal fatigue test, which may be differently set according to a material of the specimen S.

Meanwhile, in the first exemplary embodiment of the present invention, the heating part-heating step S120 may be determined through a feedback process. That is, the heating part 120 may be heated to a predetermined temperature through the heating elements 122 installed on the heating part 120, and when a temperature of the heating part 120 reaches the predetermined temperature, the heating of the heating part 120 through the heating elements 122 may be stopped.

In this case, the temperature of the heating part 120 may be continuously measured using a separate temperature measuring device. When the temperature of the heating part 120 is lowered to a predetermined temperature or less, the heating part 120 may be heated to the predetermined temperature through the heating elements 122 of the heating part 120. Such an operation may be repeatedly performed, and the temperature of the heating part 120 may be maintained within a range of the predetermined temperature.

Meanwhile, the first exemplary embodiment of the present invention describes that the heating part-heating step S120 is performed after the specimen-installing step S110, but is not limited thereto. If necessary, the heating part-heating step S120 may be first performed prior to the specimen-installing step S110.

The specimen-heating step S130 is a step to allow the specimen S to move along the heating section R1 and to heat the specimen S by rotating the rotating member 110. Here, the specimen S may be preferably heated to the temperature of the heating part 120.

Meanwhile, the rotational speed and the rotational direction of the rotating member 110 may be controlled by the controller 140 to thereby adjust a time for which the specimen S moves along the heating section within the heating part 120.

The specimen-cooling step S140 is a step to allow the specimen S to move along the cooling section R2 and to cool the specimen S by rotating the rotating member 110. Here, the specimen S may be preferably cooled to an initial temperature thereof from the predetermined temperature.

In addition, in the specimen-cooling step S140, the specimen S may be gradually cooled through the ambient air. However, if necessary, the specimen S may be rapidly cooled by spraying water, compressed air, or a combination thereof toward the specimen S.

Meanwhile, in the case that a heating time of the specimen S is changed by the controller 140 in the specimen-heating step S130, it may be preferable to adjust a cooling time of the specimen S by the controller 140 in the specimen-cooling step S140, in the same manner to the case of the specimen-heating step S130.

The repeating step S150 is a step to repeat the specimen-heating step S130 and the specimen-cooling step S140 until the coating of the specimen S is delaminated. In the method S100 for continuously testing thermal fatigue according to the first exemplary embodiment of the present invention, various methods may be present, but a time at which the coating of the specimen S is delaminated is considered as a completion time of the thermal fatigue test.

Thus, through the repeating step S150, a repeated number of times of the specimen-heating step S130 and the specimen-cooling step S140 may be measured, whereby thermal fatigue characteristics of the specimen S may be measured.

Next, an apparatus 200 for continuously testing thermal fatigue according to a second exemplary embodiment of the present invention will be described.

Figure 9:
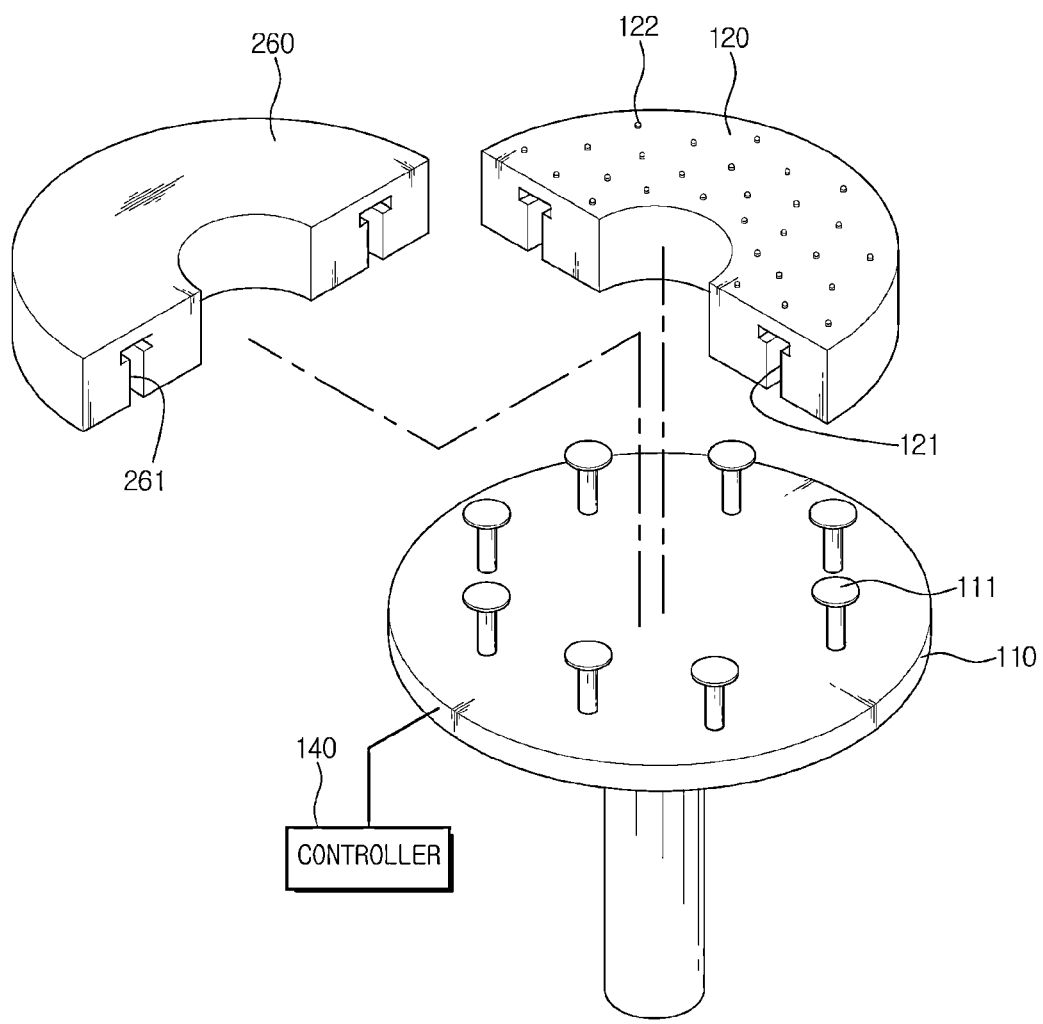
FIG. 9 is an exploded perspective view schematically illustrating an apparatus for continuously testing thermal fatigue according to a second exemplary embodiment of the present invention.

FIG. 9 is an exploded perspective view schematically illustrating an apparatus for continuously testing thermal fatigue according to a second exemplary embodiment of the present invention.

Referring to FIG. 9, the apparatus 200 for continuously testing thermal fatigue according to the second exemplary embodiment of the present invention may simultaneously perform a thermal fatigue test on a plurality of specimens, and may include the rotating member 110, the heating part 120, the air-curtain formation part 130, the controller 140, and a cooling part 260.

Since the rotating member 110, the heating part 120, the air-curtain formation part 130, and the controller 140 are substantially identical to those described in the first exemplary embodiment as described above, a detailed description will be omitted herein.

Meanwhile, the apparatus 200 for continuously testing thermal fatigue according to the second exemplary embodiment of the present invention is significantly different from the apparatus 100 for continuously testing thermal fatigue according to the first exemplary embodiment of the present invention, in that it further includes the cooling part 260 besides the cooling fluid spraying part 150.

The cooling part 260 receives the cooling section R2 therein and is provided with a cooling groove 261 inwardly recessed from a surface of the cooling part 260 which faces the rotating member 110 on the rotating path of the specimen S so as to cool the specimen S in the interior of the cooling part 260.

That is, in the first exemplary embodiment of the present invention, the cooling section R2 may be outwardly exposed, such that the specimen S may be cooled by spraying external air or forcibly spraying water, compressed air or a combination of water and compressed air to the specimen S. On the other hand, in the second exemplary embodiment of the present invention, a separate member which is cooled to a predetermined temperature may be provided in the cooling section R2, whereby the specimen S may be cooled.

Here, the cooling part 260 may be provided as a member through which cooling water or cooling gas having a predetermined temperature may flow.

In addition, the cooling part 260 may be formed of a transparent material, such that a time at which the coating of the specimen S is delaminated may be checked.

Meanwhile, the apparatus 200 for continuously testing thermal fatigue according to the second exemplary embodiment of the present invention may further include an insulating layer (not shown) on the surface where the heating part 120 and the cooling part 260 face each other in order to block a thermal transfer between the heating part 120 and the cooling part 260.

As set forth above, according to exemplary embodiments of the present invention, an apparatus for continuously testing thermal fatigue, capable of simultaneously performing a thermal fatigue test on a plurality of specimens to allow for a significant decrease in time required for testing thermal fatigue, may be provided.

In addition, a thermal fatigue test on the specimens may be conducted through a simple method.

While exemplary embodiments have been shown and described above, it will be apparent to those skilled in the art that modifications and variations could be made without departing from the spirit and scope of the present invention as defined by the appended claims.

LIST OF REFERENCE NUMERALS

100: apparatus for continuously testing thermal fatigue
S: specimen
100: rotating member
120: heating part
130: air-curtain formation part
140: controller
150: cooling fluid spraying part
200: apparatus for continuously testing thermal fatigue
260: cooling part
S100: method for continuously testing thermal fatigue
S110: specimen-installing step
S120: heating part-heating step
S130: specimen-heating step
S140: specimen-cooling step
S150: repeating step

What is claimed is:

1. An apparatus for continuously testing thermal fatigue, the apparatus comprising:
    a rotating member which is rotated about a central axis and which is provided with a plurality of protrusions outwardly protruded from an outer surface of the rotating member, the plurality of protrusions being formed along a virtual circle having a central portion passing through the central axis and coated specimens being installed on the end portion of the protrusions; and
    a heating part which is provided to receive a portion of a rotating path of the specimens therein and which is provided with a heating groove inwardly recessed from a surface of the heating part facing the rotating member along the rotating path of the specimens so as to heat the specimens within the heating part,
    wherein the rotating path of the specimens includes a heating section which is received in the heating groove and a cooling section which is not received in the heating groove.

2. The apparatus of claim 1, wherein the heating groove is provided with an inlet into which the specimens in a cooled state are introduced and an outlet from which the specimens in a heated state are discharged, and
    the apparatus further includes an air-curtain formation part which is disposed on at least one of the inlet and the outlet to form an air-curtain so as to minimize the occurrence of a thermal transfer through the heating groove.

3. The apparatus of claim 1, further comprising: a controller which controls at least one of a rotational speed and a rotational direction of the rotating member.

4. The apparatus of claim 3, wherein the rotating member is sequentially rotated in one direction or an opposite direction thereto by the controller.

5. The apparatus of claim 1, wherein the heating part is provided as a plurality of heating parts which are spaced apart from each other along a rotating path of the protrusions, and
    the cooling section is formed in each space between the plurality of heating parts.

6. The apparatus of claim 1, wherein the protrusions are formed along virtual circles which have a common central portion passing through the central axis while having different diameters, and the heating groove is provided as a plurality of grooves which are formed to be spaced apart from each other in a direction toward a central portion of the heating part or in a radial direction so as to correspond to the protrusions.

7. The apparatus of claim 1, further comprising: a cooling fluid spraying part which sprays a cooling fluid to the cooling section so as to cool the specimens on the cooling section.

8. The apparatus of claim 2, further comprising: a cooling fluid spraying part which sprays a cooling fluid to the cooling section so as to cool the specimens on the cooling section.

9. The apparatus of claim 3, further comprising: a cooling fluid spraying part which sprays a cooling fluid to the cooling section so as to cool the specimens on the cooling section.

10. The apparatus of claim 4, further comprising: a cooling fluid spraying part which sprays a cooling fluid to the cooling section so as to cool the specimens on the cooling section.

11. The apparatus of claim 5, further comprising: a cooling fluid spraying part which sprays a cooling fluid to the cooling section so as to cool the specimens on the cooling section.

12. The apparatus of claim 6, further comprising: a cooling fluid spraying part which sprays a cooling fluid to the cooling section so as to cool the specimens on the cooling section.

13. The apparatus of claim 7, wherein the cooling fluid spraying part sprays water or compressed air, or simultaneously sprays water and compressed air.

14. The apparatus of claim 1, further comprising: a cooling part which receives the cooling section therein and which is provided with a cooling groove inwardly recessed from a surface of the cooling part which faces the rotating member along the rotating path of the specimens so as to cool the specimens within the cooling part.

15. The apparatus of claim 2, further comprising: a cooling part which receives the cooling section therein and which is provided with a cooling groove inwardly recessed from a surface of the cooling part which faces the rotating member along the rotating path of the specimens so as to cool the specimens within the cooling part.

16. The apparatus of claim 3, further comprising: a cooling part which receives the cooling section therein and which is provided with a cooling groove inwardly recessed from a surface of the cooling part which faces the rotating member along the rotating path of the specimens so as to cool the specimens within the cooling part.

17. The apparatus of claim 4, further comprising: a cooling part which receives the cooling section therein and which is provided with a cooling groove inwardly recessed from a surface of the cooling part which faces the rotating member along the rotating path of the specimens so as to cool the specimens within the cooling part.

18. The apparatus of claim 5, further comprising: a cooling part which receives the cooling section therein and which is provided with a cooling groove inwardly recessed from a surface of the cooling part which faces the rotating member along the rotating path of the specimens so as to cool the specimens within the cooling part.

19. The apparatus of claim 6, further comprising: a cooling part which receives the cooling section therein and which is provided with a cooling groove inwardly recessed from a surface of the cooling part which faces the rotating member along the rotating path of the specimens so as to cool the specimens within the cooling part.

* * * * *